(12) United States Patent
Bhave et al.

(10) Patent No.: US 9,877,853 B2
(45) Date of Patent: Jan. 30, 2018

(54) STENT HAVING ADDED FEATURE FOR STRAIN RELIEF AND MITIGATION OF CRACK PROPAGATION

(71) Applicant: BOSTON SCIENTIFIC SCIMED, INC., Maple Grove, MN (US)

(72) Inventors: Aparna Bhave, Woodbury, MN (US); Dennis A. Boismier, Shorewood, MN (US); Paul F. Chouinard, Maple Grove, MN (US); Shelley Thurk, Rogers, MN (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 0 days.

(21) Appl. No.: 15/087,058

(22) Filed: Mar. 31, 2016

(65) Prior Publication Data

US 2016/0287417 A1 Oct. 6, 2016

Related U.S. Application Data

(60) Provisional application No. 62/142,187, filed on Apr. 2, 2015.

(51) Int. Cl.
*A61F 2/06* (2013.01)
*A61F 2/89* (2013.01)
*A61F 2/915* (2013.01)

(52) U.S. Cl.
CPC ............. *A61F 2/89* (2013.01); *A61F 2/915* (2013.01); *A61F 2002/91575* (2013.01); *A61F 2210/0004* (2013.01); *A61F 2250/0067* (2013.01); *A61F 2250/0098* (2013.01)

(58) Field of Classification Search
CPC combination set(s) only.
See application file for complete search history.

(56) References Cited

U.S. PATENT DOCUMENTS

2006/0271170 A1 11/2006 Gale et al.

FOREIGN PATENT DOCUMENTS

WO 03047463 A1 6/2003
WO 2007005800 A1 1/2007

*Primary Examiner* — Thomas J Sweet
*Assistant Examiner* — Tiffany Shipmon
(74) *Attorney, Agent, or Firm* — Seager, Tufte & Wickhem, LLP

(57) ABSTRACT

A bioabsorbable stent comprises a plurality of struts interconnected by a plurality of curved intersections. Each of the plurality of curved intersections defines a crescent shaped opening therethrough. The stent has a manufactured state, a crimped state and an expanded state. The crescent shaped openings each have a width and a length such that in the crimped state the width of the crescent shaped opening is less than the width of the crescent shaped opening in the manufactured state or the expanded state.

19 Claims, 5 Drawing Sheets

STENT HAVING ADDED FEATURE FOR STRAIN RELIEF AND MITIGATION OF CRACK PROPAGATION

CROSS-REFERENCE TO RELATED APPLICATIONS

This application claims priority under 35 U.S.C. §119 to U.S. Provisional Application Ser. No. 62/142,187, filed Apr. 2, 2015, the entirety of which is incorporated herein by reference.

BACKGROUND OF THE INVENTION

The present invention relates generally to implantable medical devices, and more particularly, to stents, and even more particularly, to bioabsorbable stents. As used herein the term stent refers to any type of expandable frame work, scaffold or implantable prosthesis for providing support to a body lumen.

Stents are used for a variety of medical purposes in the body including in the coronary arteries, the peripheral arteries, arteries of the neck, cerebral arteries, veins, biliary ducts, urethras, ureters, fallopian tubes, bronchial tubes, the trachea, the esophagus and the prostate.

Stents are typically placed or implanted within a bodily vessel, for example, for treating stenoses, strictures or aneurysms therein. They are implanted to reinforce sections of a blood vessel that are collapsing, partially occluded, weakened, or dilated.

Stents are radially expandable and are typically available in self-expanding configuration and mechanically expandable configuration.

Many stents are manufactured with struts having a zig-zag or serpentine configuration which resembles that of a sine wave, and are described as having a plurality of struts interconnected by peaks and troughs, or by curved intersections.

The peaks and troughs, or generally the curved intersections, in a coronary stent or scaffold are the locations that typically experience a high degree of deformation due to crimping and expansion, as well as the greatest periodic strain due to arterial pulsations. These peaks can develop fractures that often start as a crack in the inner peak and propagate outwards.

For bioabsorbable stents or scaffolds, fractures that occur in a couple of months or less after implantation are suspected to result in higher levels of restenosis or stent thrombosis.

Studies have shown that micro-fractures can be observed in some of the higher strain areas of the stent, including many initiating from the inner peak radius of the peaks interconnecting the stent struts. These micro-fractures can further develop into cracks which propagate outward towards the outer portion of the peak or intersection of the stent struts.

Studies have also established that with many bioabsorbable materials, higher strains can result in accelerated material degradation. This can manifest in the form of cracks that can propagate through the width of the strut or peak leading to fracture.

There remains a need in the art for a bioabsorbable stent having improved strain relief and a mechanism for preventing or stopping crack propagation.

Without limiting the scope of the invention a brief summary of some of the claimed embodiments of the present disclosure is set forth below. Additional details of the summarized embodiments of the invention and/or additional embodiments of the present disclosure may be found in the Detailed Description of the Invention.

SUMMARY OF THE INVENTION

In one aspect, the present invention relates to a radially expandable bioabsorbable stent comprising a plurality of struts interconnected by a plurality of curved intersections. Each of the plurality of curved intersections define a crescent shaped opening therethrough.

The stent has a manufactured state, a crimped state and an expanded state; such that the diameter of the stent in the manufactured state may be reduced as the stent is "crimped" onto a delivery system. The stent may be radially expanded from the crimped state to the greater diameter of the expanded state. The crescent shaped openings have a width and a length, in the crimped state the width of the crescent shaped opening is less than the width of the crescent shaped opening in the manufactured state or in the expanded state.

The bioabsorbable stent may have the crescent shaped opening positioned in between an inner portion and an outer portion of each of the plurality of the curved intersections.

The bioabsorbable stent may have the crescent shaped opening positioned closer to an inner portion of each of the plurality of curved intersections than to an outer portion of the curved intersections.

The bioabsorbable stent may have a plurality of crescent shaped openings positioned in a given curved intersection.

The stent may be formed from a member selected from poly(α-hydroxy acid), polyglycolide, poly-L-lactide, poly-D-lactide, poly-DL-lactide, polylactide-co-glycolide (PLGA), polycaprolactone (PCL), copolymers and terpolymers thereof, and mixtures thereof. The stent may also be formed from composites of any of the above materials with additives added to increase the strength of the composite matrix.

The stent may also include a drug eluting coating disposed thereon.

The stent may include a drug eluting coating having a bioabsorbable polymer.

The stent may include a drug eluting coating including a drug selected from the "olimus" drug analogues.

The stent may include a drug eluting coating wherein the drug is everolimus or paclitaxel.

The stent may include a crescent shaped opening formed of a plurality of slots or perforations having stent wall disposed therebetween.

The stent may include radiopaque markers.

The stent may include radiopaque markers located at a distal end of the stent, a proximal end of the stent, or both.

The stent may, in the expanded state, exhibit cracks that do not extend beyond an inner portion of the curved intersections.

In another aspect, the present invention relates to a method of providing strain relief to arrest crack propagation in high strain areas of a stent, the stent having a manufactured state, a crimped state and an expanded state. The method comprises providing an elongate tube, forming a pattern in the elongate tube, the pattern consisting of a plurality of struts interconnected by curved intersections and cutting a crescent shaped opening in the curved intersections, wherein the crescent shaped opening is defined thereby. In the crimped state the width of the crescent shaped opening is less than the width of the crescent shaped opening in the manufactured state and in the expanded state, and wherein the high strain areas are located on an inner portion of the curved intersections, the crescent shaped opening providing strain relief in the crimped state and limiting crack formation to the inner portion of the curved intersection.

The method may include forming the pattern of struts and curved intersections in the elongate tube by laser cutting.

The method may include cutting a crescent shaped opening in the curved intersections comprising laser cutting.

The method may include forming the crescent shaped opening in the curved intersections at a location that is closer to the inner portion of the curved intersections than to the outer portion of the curved intersections.

These and other aspects of an integral balloon shaft, a balloon catheter, methods of making an integral balloon shaft, and methods of making the balloon catheter are pointed out with particularity in the claims annexed hereto and forming a part hereof. However, for further understanding reference can be made to the drawings which form a further part hereof and the accompanying descriptive matter, in which one or more embodiments are illustrated and described.

DETAILED DESCRIPTION OF THE INVENTION

Figure 1:
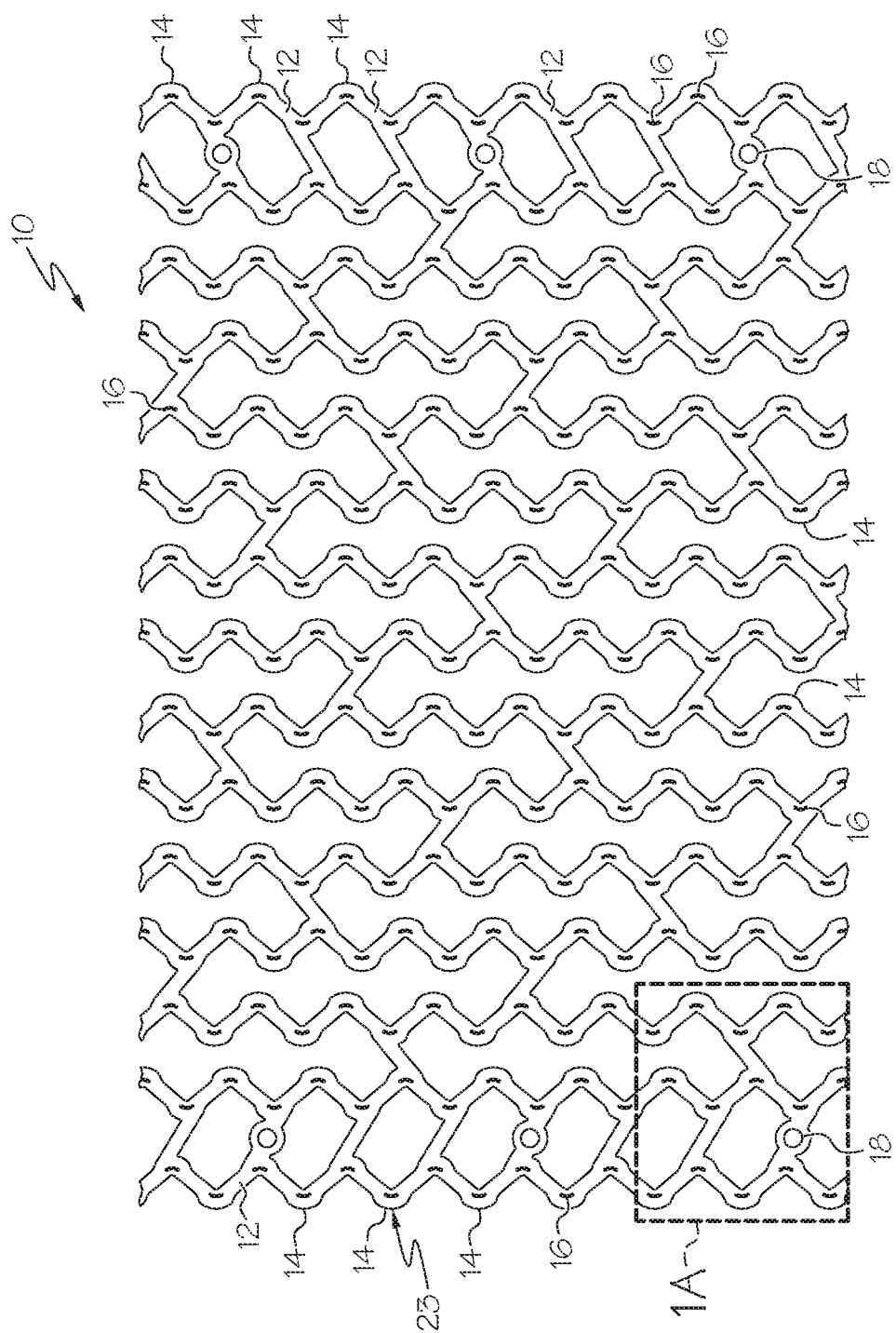
FIG. 1 is a flat view of a stent according to the invention.

While the subject matter of the present disclosure may be embodied in many different forms, there are described in detail herein specific preferred embodiments of the present disclosure. This description is an exemplification of the principles of the present disclosure and is not intended to limit the present disclosure to the particular embodiments illustrated.

For the purposes of this disclosure, like reference numerals in the figures shall refer to like features unless otherwise indicated.

Turning now to the figures, FIG. 1 is a flat view of the stent 10 according to the invention. Stent 10 includes a plurality of struts 12 interconnected by curved intersections 14, also referred to in the art as "peaks" and "valleys" or "troughs". The curved intersections 14 include curved openings 16 therethrough. These curved openings 16, which also may be referred to as small windows, slots or holes, are cut out of the peak, troughs or other areas of intersection to provide strain relief and to cause a propagating crack to be halted or blunted within the opening 16 rather than propagating upward toward the outer surface 23 of the curved intersection 14.

In this embodiment, the curved openings are crescent shaped. In other embodiments, the openings 16 may be provided with any shape configured to correspond to the shape and performance characteristics of the intersection 14 into which they are formed.

Stent 10 also includes radiopaque markers 18 located at the distal end and the proximal end of the stent. Radiopaque markers can be included at one of the proximal end, distal end, or both, as well as on any other portion of the stent as well. Markers 18 may be constructed of any radiopaque material desired. Examples of suitable materials for inclusion in the construction of markers 18 may include platinum, iridium, gold, palladium, and/or other materials. In at least one embodiment, markers 18 are comprised of platinum or platinum alloy. Markers 18 may be configured to remain within the vessel that the stent 10 is deployed in, even after the remainder of the stent structure has been absorbed or degraded away.

Figure 1A:
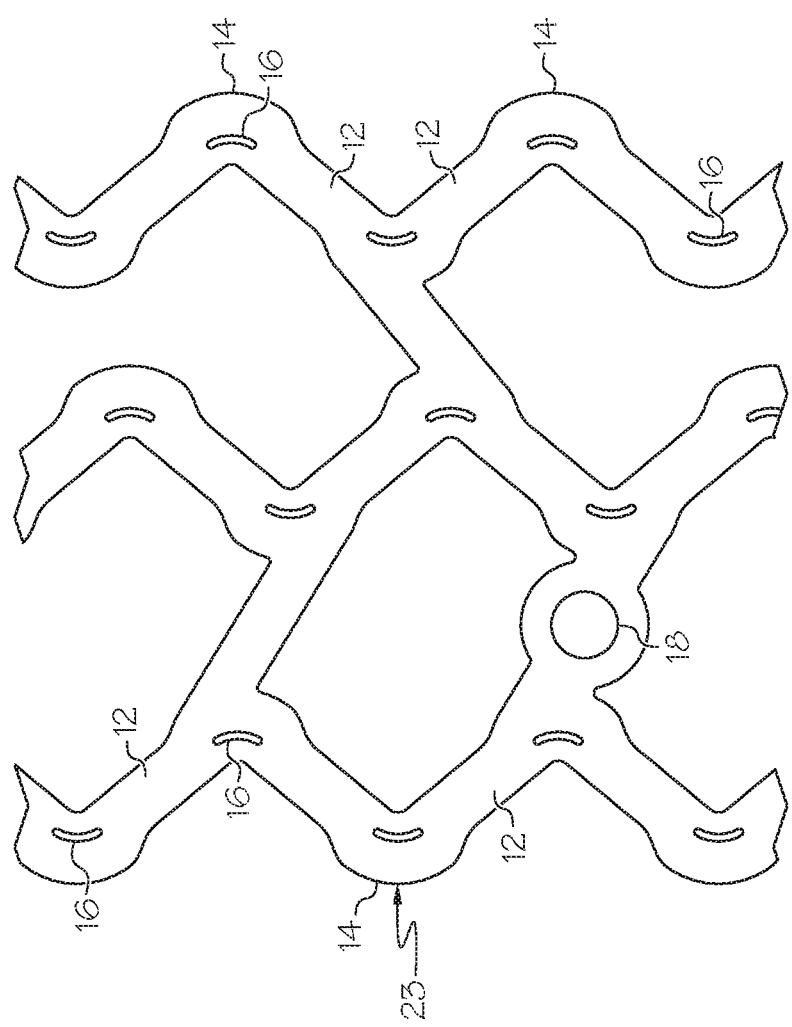
FIG. 1A is an enlarged portion of the stent taken at section 1A in FIG. 1.

FIG. 1A is an enlarged view of the portion of stent 10 taken at section 1A in FIG. 1.

Figure 2C:
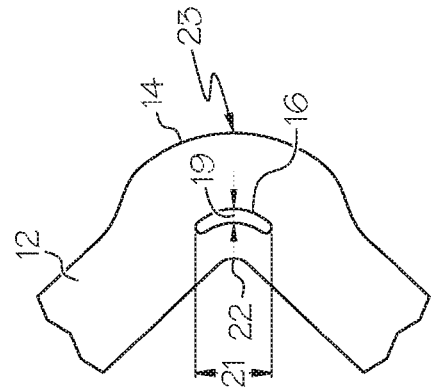
FIG. 2C is a partial view of the struts interconnected by the curved intersection in the expanded state of the stent.
Figure 2B:
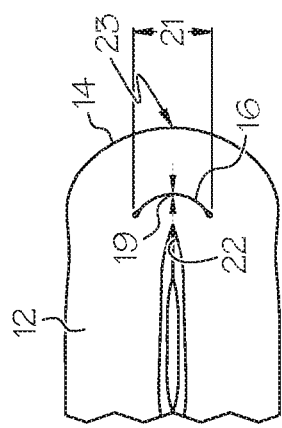
FIG. 2B is a partial view of the struts interconnected by the curved intersection in the crimped state of the stent.
Figure 2A:
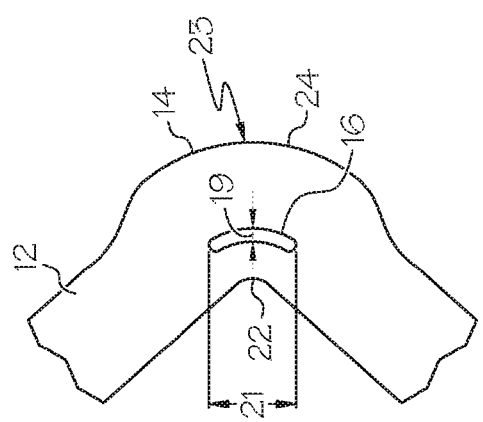
FIG. 2A is a partial view of the struts interconnected by a curved intersection in the manufactured state of the stent.

FIG. 2A is a view of struts 12 interconnected by curved intersection 14 when the stent is in a manufactured state, the curved intersection having a crescent shaped opening 16 therethrough, defined by a width 19 and length 21.

FIG. 2B is a view of struts 12 interconnected by curved intersections 14 when the stent 10 is in a crimped state.

FIG. 2C is a view of struts 12 interconnected by curved intersections 14 when the stent 10 is in the expanded state.

As is shown in FIGS. 2A-2C, the width of the crescent shaped opening 16 when the stent is in the expanded state (see FIG. 2C) and the manufactured state (see FIG. 2A) is greater than the width of the crescent shaped opening 16 when the stent is in the crimped state (see FIG. 2B). In some embodiments, the stent in the manufactured state has openings 16 having a width 19 of about 30 µm to about 20 µm. In some embodiments, when the stent 10 is in the crimped state the width 19 of the opening 16 may be less than or equal to about 5 µm. In some embodiments the width 19 in the crimped state may be zero µm; that is to say the opening 16 is essentially closed in the crimped state.

Figure 3:
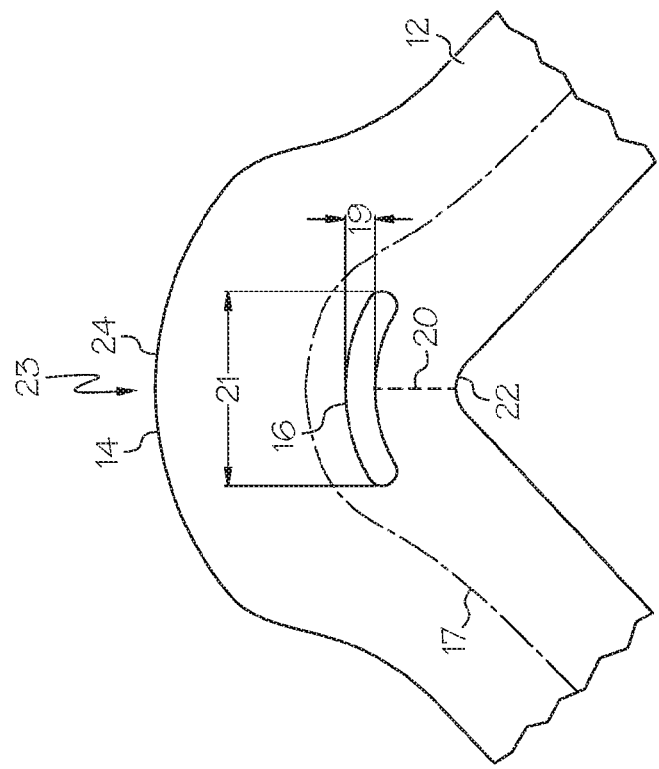
FIG. 3 is a partial view of the stent struts interconnected by the curved intersection and illustrates the position of an opening within the inner portion of the curved intersection and the manner in which the opening limits fracture formation to the inner portion of the curved intersection.

The position, size, shape and number of the opening 16 within the intersection 14 may vary. In at least one embodiment, such as is shown in FIG. 3 the curved intersection 14 may be viewed as having a center line 17 which divides the intersection 14 into an inner portion 22 and an outer portion 24. In this embodiment the crescent shaped opening 16 is located closer to the inner portion 22 of the curved intersection 14 than to the outer portion 24 of the curved intersection 14. In the embodiment shown in FIG. 4, multiple openings 16 are provided in the inner portion 22 of the intersection 14.

It has been observed that fractures and crack propagation (indicated by line 20 in FIG. 3) more typically occurs at inner portion 22 of the curved intersection 12. By positioning the opening 16 in the manner shown, the formation of a crack is limited to only a fracture within the inner portion 22 of the intersection 14, as the fracture cannot propagate beyond the opening 16.

Figure 4:
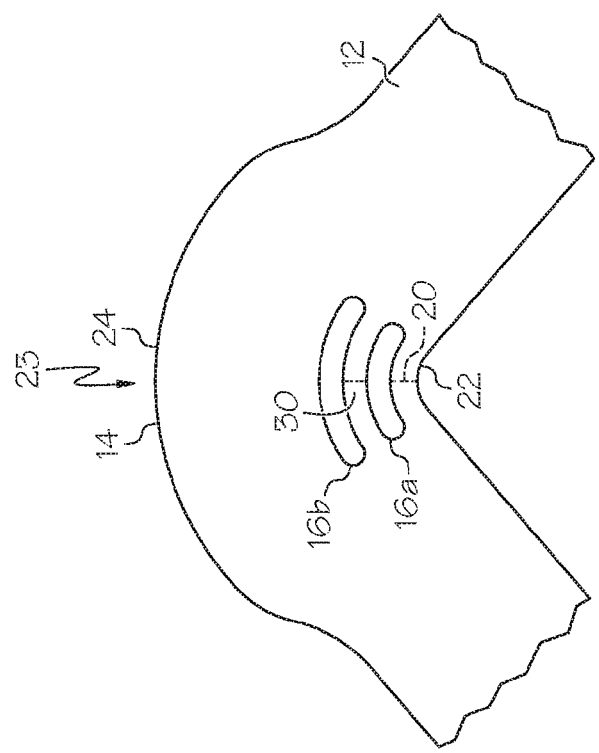
FIG. 4 is a partial view of the stent struts interconnected by the curved intersection and illustrates an embodiment wherein the curved intersection defines a plurality of openings therethrough.

In the case of FIG. 4, where multiple openings 16a and 16b are provided, the multiple openings provide additional strain relief and serve as a multi-point fracture stop. Should a crack 20 propagate to the first opening 16a, the ligament 30 positioned between the first opening 16a and the second opening 16b serves as additional structural strength until the crack 20 makes its way to the second opening 16b. The second opening 16b then provides a smooth surface which delays or prevents crack propagation through the outer portion 24 of the intersection.

High strain on the inner portion 22 of the curved intersections 14 typically occurs as a result of crimping (see FIG. 2B). Damage may be caused to the inner portion 22 of the curved intersections 14 during crimping. The pulsation of the coronary arteries after implantation of the stent may cause initiation of a crack that may propagate and eventually lead to full fracture of the peak. The crescent shaped openings 16 can reduce the damage/defects that may be caused during crimping by providing strain relief, reducing the likelihood of crack formation and provide a mechanism to arrest the propagation of the crack at the openings 16.

Pre-clinical trials indicate that the stents according to the invention exhibit far less fracturing, as compared to control stents that lacked the openings 16.

A pattern including struts and curved intersections can be formed in a tubular member using standard laser cutting methods. Other mechanisms of opening formation such as formation by the use of dies, mechanical drilling, or other mechanisms may also be utilized.

The position of the crescent shaped opening is adjusted in the curved intersection to provide optimal radial strength of the stent. Preferably, the position of the opening is as close to the inner peak as possible for the manufacturing technique (s) utilized.

While crescent shaped openings have been embodied herein, other shapes can be employed without departing from the scope of the present invention.

Stents may be formed from any material, and in at least one embodiment the stent is comprised of a bioabsorbable material including, but not limited to poly(α-hydroxy acid) homopolymers, poly(α-hydroxy acid) copolymers, polyglycolide, poly-L-lactide, poly-D-lactide, lactide, poly-DL-lactide, and mixtures thereof. Stents may be partially or wholly bioabsorbable. Stents may be made of composites of the aforementioned materials. Such composite materials may include additives for strengthening or otherwise modifying the various characteristics of the stent material.

The stents may include a drug eluting coating disposed on at least a portion of the surface of the stent.

Drug coatings may include a polymer and a therapeutic drug, applied to the stent out of a solvent solution.

Suitably, the polymer is also bioabsorbable but may also be non-absorbable.

The polymer may be the same, or different than that from which the stent is formed including, but not limited to poly(α-hydroxy acid) homopolymers, poly(α-hydroxy acid) copolymers, polyglycolide, poly-L-lactide, poly-D-lactide, poly-DL-lactide, and mixtures and copolymers thereof.

In some embodiments, the stent is formed from a semi-crystalline poly-L-lactide (PLLA).

Drugs or therapeutic agents employed on stents or other implantable or insertable medical devices are well known in the art.

The drug may be an anti-proliferative and/or an anti-inflammatory, for example.

The drug may be selected from a vast array of drugs and examples include, but are not limited to, rapamycin analogues, olimus analogues such as macrolide antibiotics including but not limited to, biolimus, everolimus, zotarolimus, tenmsirolimus, picrolimus, novolimus, myolimus, all taxoids such as taxols, docetaxel, and paclitaxel, paclitaxel derivatives, and so forth.

Examples of drugs include the "olimus" family analogues.

In some embodiments the drug is everolimus.

In some embodiments the drug is paclitaxel.

These lists are not exhaustive but are intended for illustrative purposes only, and not as a limitation on the scope of the present invention. Other suitable substitutes may be selected by those of ordinary skill in the art without departing from the scope of the present invention.

EXAMPLES

Stents were formed using standard laser cutting methods with a stent pattern as shown in FIG. 1, for example including struts interconnected by curved intersections.

Examples

Figure 5:
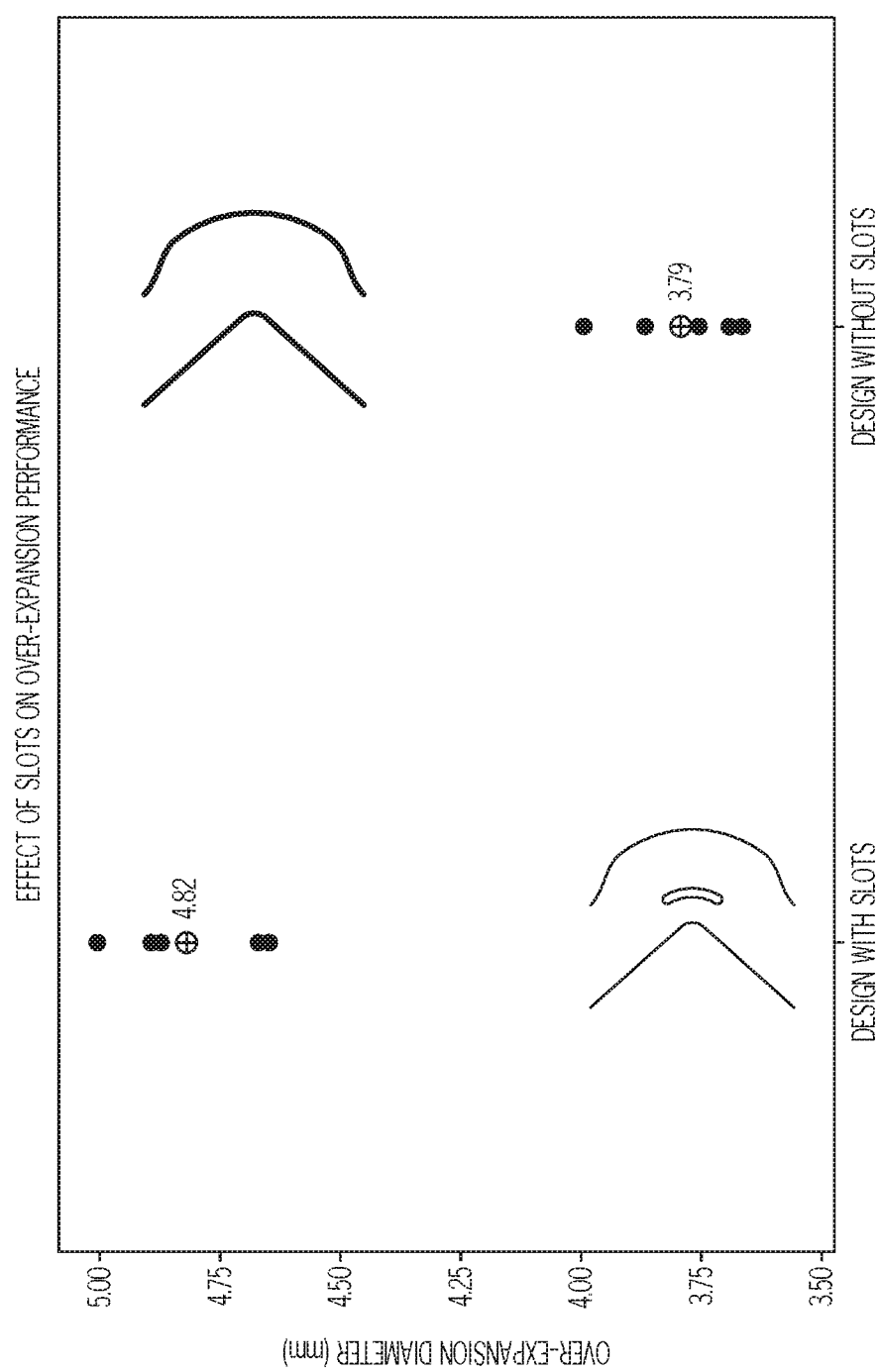
FIG. 5 is a graph illustrating over-expansion performance of a prior art stent and over-expansion of a stent according to the invention.

FIG. 5 is a graph illustrating over-expansion of a stent having the openings in the curved intersection therethrough and a stent having no openings. Where a strut intersection 14 is provided with the crescent shaped opening 16, stent 10 can achieve a greater level of over-expansion than a design without openings 16. In five tests an embodiment of the stent 10 was capable of achieving an average inner diameter of 4.82 mm whereas a stent without openings averaged an inner diameter of 3.79 mm. In addition, tests have shown that where stents of similar geometry and composition are crimped and subsequently expanded to a predetermined diameter, there is an appreciably greater presence of cracks and crazing in stents having no openings of the type described herein (e.g. opening 16) as compared to stents, such stent 10 which is provided with openings 16.

The description provided herein is not to be limited in scope by the specific embodiments described which are intended as single illustrations of individual aspects of certain embodiments. The methods, compositions and devices described herein can comprise any feature described herein either alone or in combination with any other feature (s) described herein. Indeed, various modifications, in addition to those shown and described herein, will become apparent to those skilled in the art from the foregoing description and accompanying drawings using no more than routine experimentation. Such modifications and equivalents are intended to fall within the scope of the appended claims.

All publications, patents and patent applications mentioned in this specification are herein incorporated by reference in their entirety into the specification to the same extent as if each individual publication, patent or patent application was specifically and individually indicated to be incorporated herein by reference. Citation or discussion of a reference herein shall not be construed as an admission that such is prior art.

The invention claimed is:

1. A bioabsorbable stent, the bioabsorbable stent comprising:
   a plurality of struts interconnected by a plurality of curved intersections, at least some of the plurality of curved intersections defining a crescent shaped opening therethrough, the stent having a manufactured state, a crimped state and an expanded state,
   the crescent shaped opening having a width and a length, in the crimped state the width of the crescent shaped opening is less than the width of the crescent shaped opening in the manufactured state or the expanded state; and wherein the width of the crescent shaped opening in the manufactured state or the expanded state is about 20 μm to about 30 μm.

2. The bioabsorbable stent of claim 1 wherein the crescent shaped opening is positioned in each of the plurality of curved intersections.

3. The bioabsorbable stent of claim 1 wherein the crescent shaped opening is located closer to an inner portion of each of the plurality of curved intersections than to an outer portion of the curved intersections.

4. The bioabsorbable stent of claim 1 wherein the width of the crescent shaped opening in the crimped state is about 5 μm or less.

5. The bioabsorbable stent of claim 1 wherein the width of the crescent shaped opening in the crimped state is zero.

6. The bioabsorbable stent of claim 1 formed from at least one member selected from the group consisting of poly(α-hydroxy acid), polyglycolide, poly-L-lactide, poly-D-lactide, poly-DL-lactide, polycaprolactone, copolymers and terpolymers thereof, and mixtures thereof.

7. The bioabsorbable stent of claim 1 further comprising a drug eluting coating.

8. The bioabsorbable stent of claim 7 wherein the drug eluting coating comprises a bioabsorbable polymer.

9. The bioabsorbable stent of claim 7 wherein the drug eluting coating comprises a member from the group of the "limus" family analogues.

10. The bioabsorbable stent of claim 7 wherein the drug is everolimus or paclitaxel.

11. The bioabsorbable stent of claim 1 further comprising radiopaque markers.

12. The bioabsorbable stent of claim 11 wherein the radiopaque markers are located at a distal end of the stent, a proximal end of the stent, or both.

13. The bioabsorbable stent of claim 1 wherein in the expanded state, the stent exhibits a reduced number of cracks in an inner portion of the curved intersections than a stent control stent formed without any crescent shaped openings.

14. The bioabsorbable stent of claim 1 wherein the at least some of the plurality of curved intersections define a plurality of crescent shaped openings therethrough.

15. A method of providing strain relief and mitigating crack propagation in high strain areas of a bioabsorbable stent, the stent having a manufactured state, a crimped state and an expanded state, the method comprising:
    providing an elongate tube;
    forming a pattern in the elongate tube, the pattern consisting of a plurality of struts interconnected by curved intersections; and
    cutting a crescent shaped opening in at least some of the curved intersections, wherein the crescent shaped opening is defined thereby, the crescent shaped opening having a width that is greater in the manufactured state or the expanded state than in the crimped state;
    wherein the width of the crescent shaped opening in the crimped state is about 5 μm or less; and
    wherein the high strain areas are located on an inner portion of the curved intersections, and wherein the crescent shaped opening provide strain relief in the crimped state and inhibit crack propagation of any crack formed at the inner portion of the curved intersection.

16. The method of claim 15 wherein the pattern formed in the elongate tube is laser cut.

17. The method of claim 15 wherein cutting a crescent shaped opening in the curved intersections comprises laser cutting.

18. The method of claim 15 wherein the crescent shaped opening is formed in the curved intersections at a location that is closer to the inner portion of the curved intersections than to the outer portion of the curved intersections.

19. The method of claim 15 further comprising applying a drug eluting coating to at least a portion of the bioabsorbable stent.

* * * * *